United States Patent
Schorn et al.

(10) Patent No.: US 8,140,173 B2
(45) Date of Patent: Mar. 20, 2012

(54) ANCHORING DEVICE FOR SECURING INTRACRANIAL CATHETER OR LEAD WIRE TO A PATIENT'S SKULL

(75) Inventors: Greg M. Schorn, Milford, MA (US); Scott Sullivan, San Francisco, CA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1132 days.

(21) Appl. No.: 11/954,780

(22) Filed: Dec. 12, 2007

(65) Prior Publication Data

US 2009/0157157 A1     Jun. 18, 2009

(51) Int. Cl.
*A61N 1/00*     (2006.01)
(52) U.S. Cl. .......................................... 607/149; 607/45
(58) Field of Classification Search ................... 607/149
See application file for complete search history.

(56) References Cited

U.S. PATENT DOCUMENTS

| | | |
|---|---|---|
| 3,444,861 A | 5/1969 | Schulte |
| 4,328,813 A * | 5/1982 | Ray .................................. 607/139 |
| 4,397,641 A | 8/1983 | Jacobs |
| 5,464,446 A | 11/1995 | Dreessen |
| 2007/0249980 A1 | 10/2007 | Carrez |

* cited by examiner

*Primary Examiner* — Eric D. Bertram

(57) ABSTRACT

An anchor system for securing a lead to a patient's skull is disclosed. The lead is of the type that passes through a burr hole created in the patient's skull and includes a distal end which is implanted within the patient's brain at a target site. The anchor, according to a first embodiment of the invention includes a stem, an integrally formed rim plate, and a peripheral clamping structure. The clamping structure is adapted to receive and snugly hold a portion of the lead. The stem is sized and shaped to fit within the burr hole, leaving the rim plate positioned flush with the patient's skull. A flared passage is provided within the stem and rim plate so that the lead may pass through the stem and into the rim plate, at which point the lead follows the contours of the flared passage and communicates with the peripheral clamping structural. The clamping structure holds a portion of the lead so that any tension of the lead will not be transmitted past the anchor and the distal end of the lead will not become displaced from the target site. According to a second embodiment, the peripheral clamping structure includes several flexible loops that are sized and spaced from each other to allow a lead to be laced through the loops as the lead extends about the periphery of the rim plate.

16 Claims, 7 Drawing Sheets

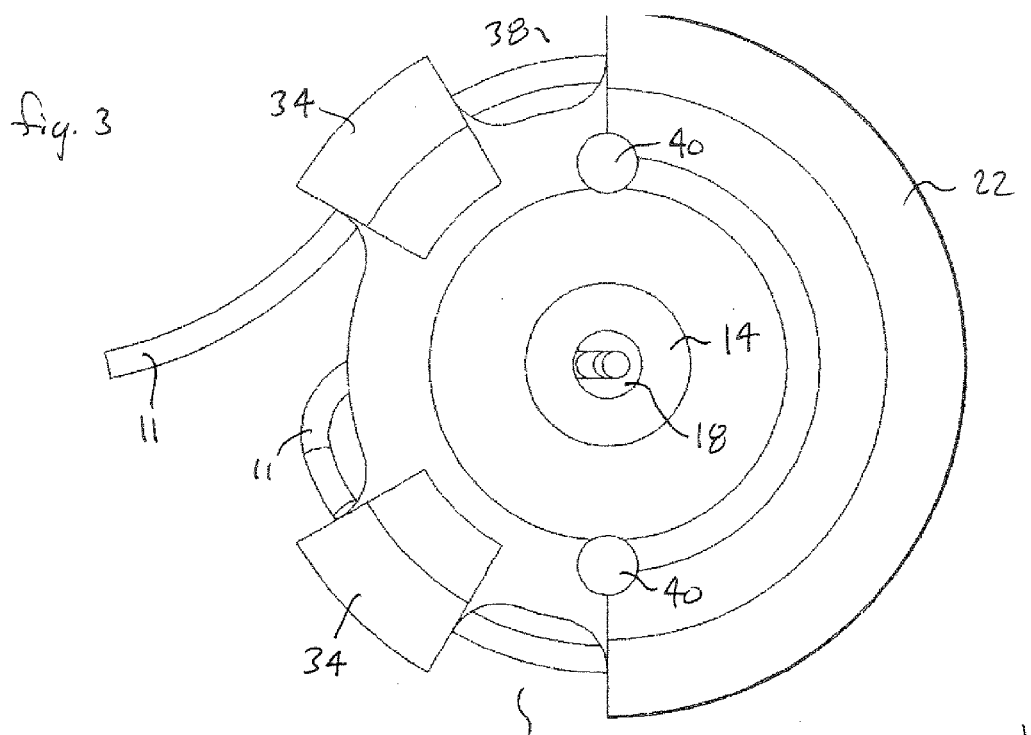
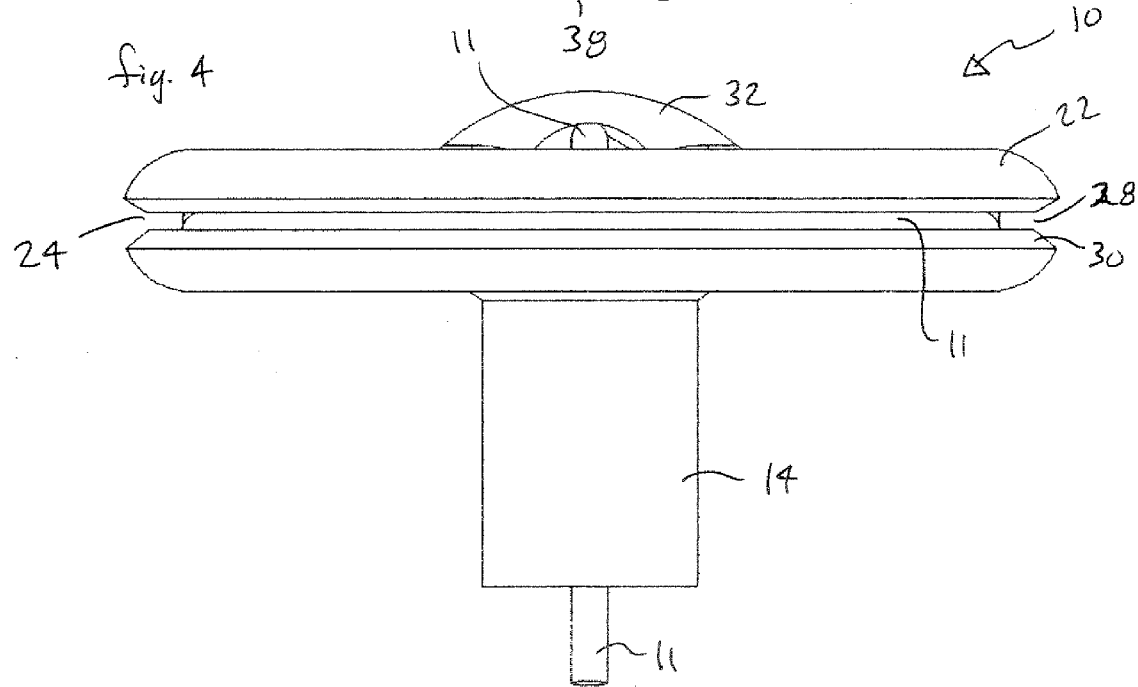

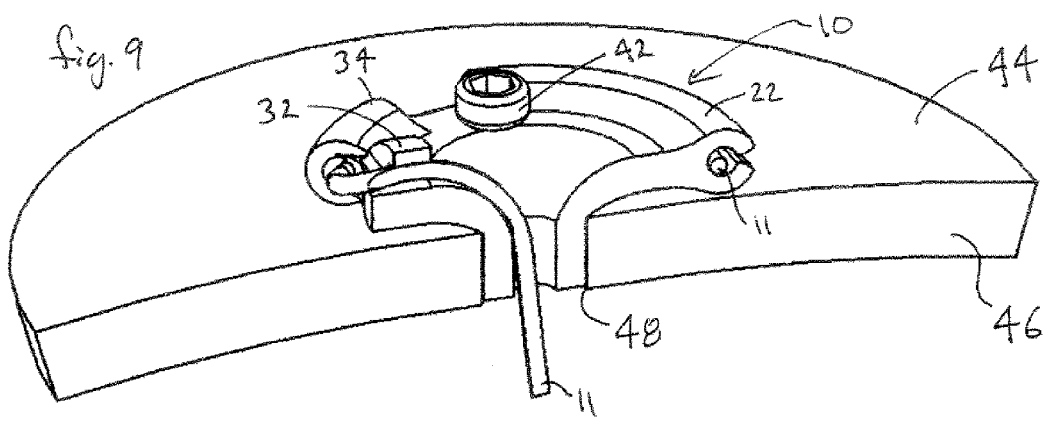
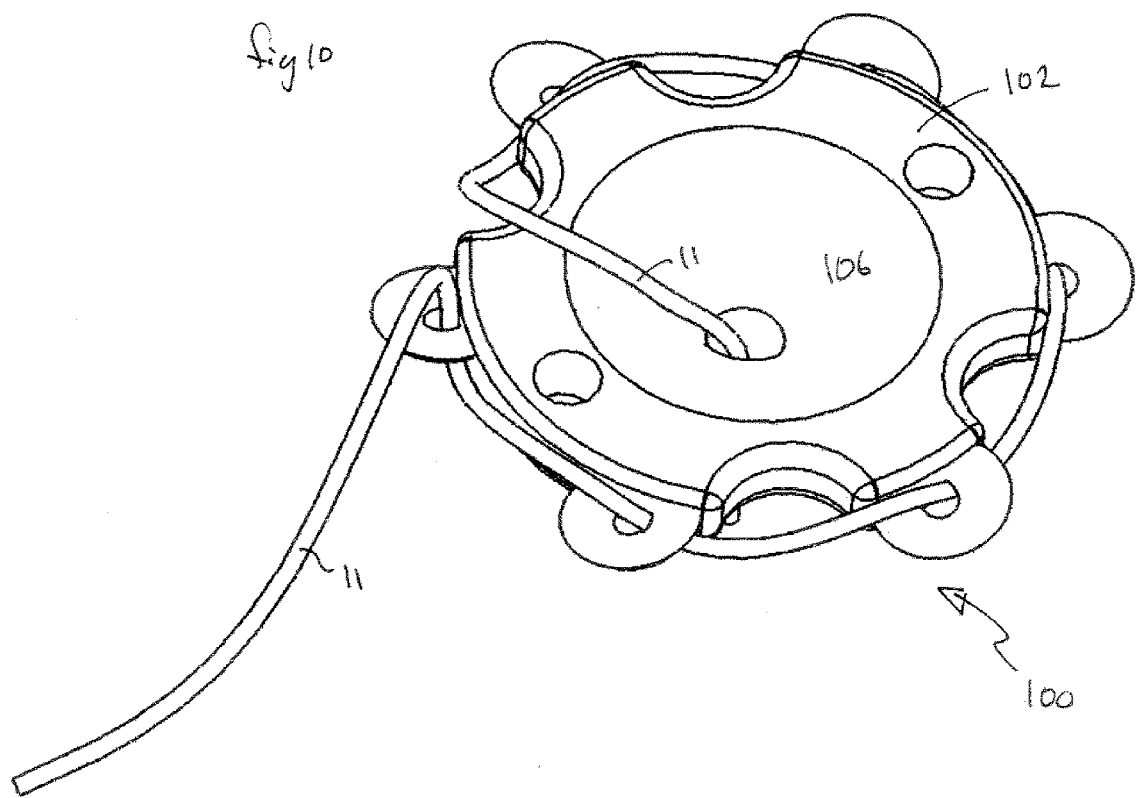

ANCHORING DEVICE FOR SECURING INTRACRANIAL CATHETER OR LEAD WIRE TO A PATIENT'S SKULL

BACKGROUND OF THE INVENTION

1. Field of the Invention

The present invention generally relates to anchoring systems for securing an implanted tubular medical device to a patient, and more particularly, to such anchoring systems for securing intracranial tubular medical devices to the patient's skull.

2. Description of the Prior Art

Surgical procedures of a patient's brain often require implanting a medical device to a prescribed intracranial target site. The implanted medical device typically requires long-term communication between the target site and a remote site located outside the patient's skull. The device can be electrically-based wherein power or signal lead wires must link the device at the target site to the outside world, or the device may be a catheter implanted to administer a drug from a remote location precisely at the target site within the brain or perhaps positioned to shunt fluid from the target site, or a catheter that includes mapping or stimulating electrodes at its distal end.

Either the electrical lead or the catheter reaches the brain by passing through a predrilled hole in the patient's skull, called a burr hole.

Electrical stimulation of the brain can be used for a variety of therapeutic treatments including relief of chronic pain and control of movement disorders. A typical electrical brain-stimulation system includes a pulse generator operatively connected to at least one electrode by a lead. The lead is connected to the electrodes at its distal end. The electrodes are implanted within the patient's brain at a precise location to optimize the applied stimulation. The lead is connected to the pulse generator at its proximal end. To prevent dislodging the implanted distal end of each electrode, a portion of the lead must be anchored in position, usually at the point of entry, the burr hole.

It is also common to use catheters to either introduce fluids (such as drugs) to or collect biological fluids from a specific target site within the patient's brain to treat brain disorders such as malignancies or neurodegenerative diseases. Another example is to position an implantable deep-brain infusion catheter in the striatum or putamen to deliver a pharmaceutical agent to treat movement disorders such as Parkinson's Disease. Typically, these implantable catheters are vary delicate being only about 1 mm to 1.5 mm in outer diameter and are therefore prone to kinking and abrasive damage during handling and especially during use over their lifetime. As with the above-described electrical application, the delicate catheter must be secured so that the distal portion of the catheter remains at the target site within the brain, regardless of the patient's movement or the movement of the catheter outside the brain, and also must prevent or at least discourage trauma that may kink or otherwise damage the catheter.

In order to insert the lead or catheter into the patient's brain, a surgeon first drills a hole in the patient's cranium using a surgical burr or a cranial perforator. The hole size will vary depending on the particular procedure being performed. The drill cuts a clean straight hole into the patient's skull and often leaves a sharp edge along the upper rim of the burr hole. Any inserted lead or catheter must be protected from this sharp edge. To do this, a burr hole ring is often inserted into the burr hole before the catheter or lead wire is inserted through the hole into the patient's brain to the target site. This ring is often used to cooperate with an insert to anchor the exiting catheter or lead wire. Previously, intracranial catheters have been sutured directly to the periosteum, which is a fibrous membrane covering the surface of bone. The periosteum does not provide as much stability as desired, and movement of the catheter anchor may result in displacement of the catheter tip.

Another method of attaching a catheter tube to a patient included the steps of first coiling the tube to form a loop, applying a strip of adhesive tape over the loop and attaching the opposite ends of each strip of tape to the patient's skin. The function of the loop was to act as a strain-relief so that the implanted distal end of the catheter tube is not displaced or disturbed even when unexpected tension is applied to the tubing.

For situations wherein an implanted intracranial medical device must remain operational for long periods of time, it is even more important to safely and effectively anchor the leads and/or catheters to a patient's skull to prevent displacement of the distal ends within the patient's brain regardless of the relative motions of these leads and/or catheters outside the patient's skull.

Obviously, a patient with such intracranial leads and/or catheters in place, whether in a hospital recovery ward, or leading an active life will invariably challenge the integrity and strength of the anchoring system. Typically, during normal patient activities, the communicating leads located outside the patient's skull will become entangled and snagged on various things and will become tugged or even violently jerked. The anchoring system must be strong enough to resist such trauma to the delicate catheter and also prevent dislodgement of the distal tip from the target site. To achieve this, current anchors are often secured directly to the patient's skull using fasteners or an appropriate adhesive or both.

One system for fixing a cranial lead is disclosed in U.S. Pat. No. 4,328,813. This patent discloses a socket and plug anchoring system wherein the lead is engaged by and held within a neck portion of the socket and recessed portion of the plug. However, in this arrangement the lead may easily be moved, particularly axially, when the plug is forced into engagement with the socket. This system uses the shape of the plug to force the exiting lead into a friction bend. This system cannot be used with catheters and any tension applied to the remote portions of the leads will act to directly remove the plug and also the socket, which will then release the lead and easily risk displacement of its distal end. This system fails to offer any strain-relief structure that allows remote applied tension to the leads to be absorbed without dislodging the implanted distal ends from the target site.

Another brain-lead anchoring system is disclosed in U.S. Pat. No. 5,464,446, "Brain Lead Anchoring System," assigned to Medtronic, Inc., which is incorporated herein by reference. The anchoring system of this referenced patent includes several parts, a plug, a cap and a socket, that must all be assembled by the surgeon and secured within the burr hole of the patient's skull and around either a lead or a catheter. A plug and socket use mere friction within the burr hole to hold the anchor and lead in place to the patient's skull. The cap covers the burr hole and allows two exiting passages. A first one is sharply angled for a lead wire and a second passage that is straight for accommodating catheters, which cannot handle the sharp bend of the first passage.

Although the anchoring system of U.S. Pat. No. 5,464,446 is versatile by allowing both a lead wire and a catheter to exit a patient's skull atraumatically, the device is too difficult to assemble, will not hold up to even moderate applied tension, and forces a catheter to exit normal to the patient's skull thereby causing difficultly in allowing the patient to perform normal activities or even hide their medical disposition—for example, the patient cannot wear a hat without potentially kinking or damaging the catheter. Also, the device of this prior art patent fails to offer a strain-relief function that can mitigate the displacement of the distal end of the implanted lead or catheter due to remote applied tension.

SUMMARY OF THE INVENTION

An object of the invention is to provide a system and method for easily and effectively securing a catheter or electrical lead from a burr hole of a patient in such a manner that ensures that the catheter or lead is anchored with respect to a target site within the patient's brain and so that tension applied to the catheter or lead will not cause damage to the same.

Another object of the invention is to provide such an anchor that safely and atruamatically redirects the exterior portion of an implanted catheter or lead wire from a perpendicular trajectory (exiting from the burr hole) to a tangential path immediately adjacent the patient's scalp.

An anchor system for securing a lead to a patient's skull is disclosed. The lead is of the type that passes through a burr hole created in the patient's skull and includes a distal end, which is implanted within the patient's brain at a target site. The anchor, according to a first embodiment of the invention includes a stem, an integrally formed rim plate, and a peripheral clamping structure. The clamping structure is adapted to receive and snugly hold a portion of the lead. The stem is sized and shaped to fit within the burr hole, leaving the rim plate positioned flush with the patient's skull. A flared passage is provided within the stem and rim plate so that the lead may pass through the stem and into the rim plate, at which point the lead follows the contours of the flared passage and communicates with the peripheral clamping structural. The clamping structure holds a portion of the lead so that any tension of the lead will not be transmitted past the anchor and the distal end of the lead will not become displaced from the target site.

According to a second embodiment, the peripheral clamping structure includes several flexible loops that are sized and spaced from each other to allow a lead to be laced through the loops as the lead extends about the periphery of the rim plate.

The accompanying drawings show examples of embodiments of the present invention. They illustrate how the invention achieves the above stated advantages and objectives.

BRIEF DESCRIPTION OF THE DRAWINGS

FIG. 3 is a bottom plan view of the lead-anchor, according to the first embodiment of the present invention, showing details of the stem with the representative lead in the anchored position;

FIG. 4 is a rear elevation view of the lead-anchor, according to the first embodiment of the present invention, showing details of the lead-encapsulating structure holding the representative lead in the anchored position;

FIG. 9 is a perspective sectional view of the lead-anchor of FIG. 8 showing details of a stem portion and the positioning of a lead wire exiting the patient's skull;

FIG. 10 is a perspective view of a lead-anchor, according to a second embodiment of the invention, showing peripheral lead-loops and a lead wire located in an anchored position;

DETAILED DESCRIPTION OF THE PREFERRED EMBODIMENTS

Figure 1:
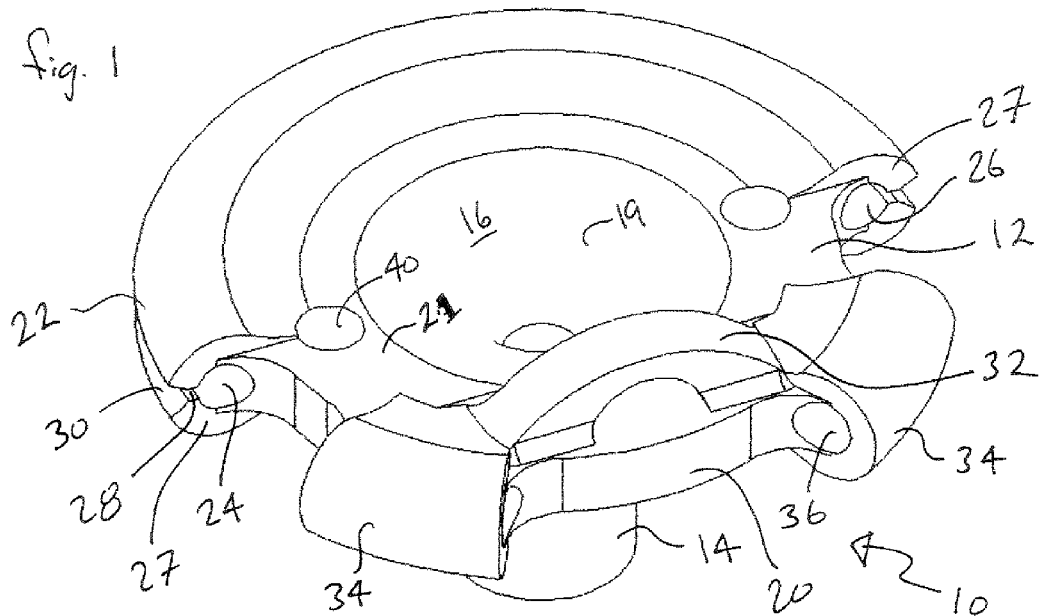
FIG. 1 is a perspective view of a lead-anchor having a rim plate, a stem, a flared passage, and a peripheral lead-encapsulating structure, according to a first embodiment of the present invention, shown without a lead or catheter in place.

At the start of the surgical procedure for implanting the distal end of either a lead wire or a catheter into a patient's brain to a target site, a carefully drilled hole (called a burr hole) having a predetermined inside diameter is formed through the patient's skull. If the lead or catheter is meant to remain at the target site for a long period of time, the portion of the lead wire or catheter that extends beyond the patient's skull will be highly susceptible to entanglement and tension which may result in an undesirable displacement of the implanted distal end from the target site. To prevent this potential displacement from occurring, the lead or catheter is typically anchored to the patient's skull. The present invention is an improved anchoring device used to secure a portion of a lead wire or a catheter leaving a burr hole formed in a patient's skull.

Referring now to FIGS. 1 through 9, a lead anchor 10 for securing communicating lead wires and catheter conduits (herein after collectively referred to as "lead 11") from intracranially implanted devices is shown, according to a first embodiment of the invention. In its basic form, as is apparent in the figures, anchor 10 is similar in shape to that of a small rubber funnel and includes a generally circular rim plate 12 and an integrally formed hollow lower stem 14. As can be seen in FIGS. 4, 5, 6, 7, and 9, lower stem 14 includes a generally cylindrical outside shape and an internal flared passage 16. Flared passage 16 connects a small lower opening 18 located at the bottom of lower stem 14 to rim plate 12 so that the flared passage 16 looks similar to the cusp shape of a trumpet horn, opening to a larger diameter at the top adjacent the rim plate 12 and defining a cusp-shaped inside surface 19. Rim plate 12 defines an upper surface 21 and a lower surface 23.

Although it is preferred that rim plate 12 be generally circular, as shown in the figures of this application, rim plate 12 can be oval or ellipsoid in plan-view shape without departing from the invention. For the purposes of explaining the present invention, the rim plate 12 will be considered circular in shape.

Figure 2:
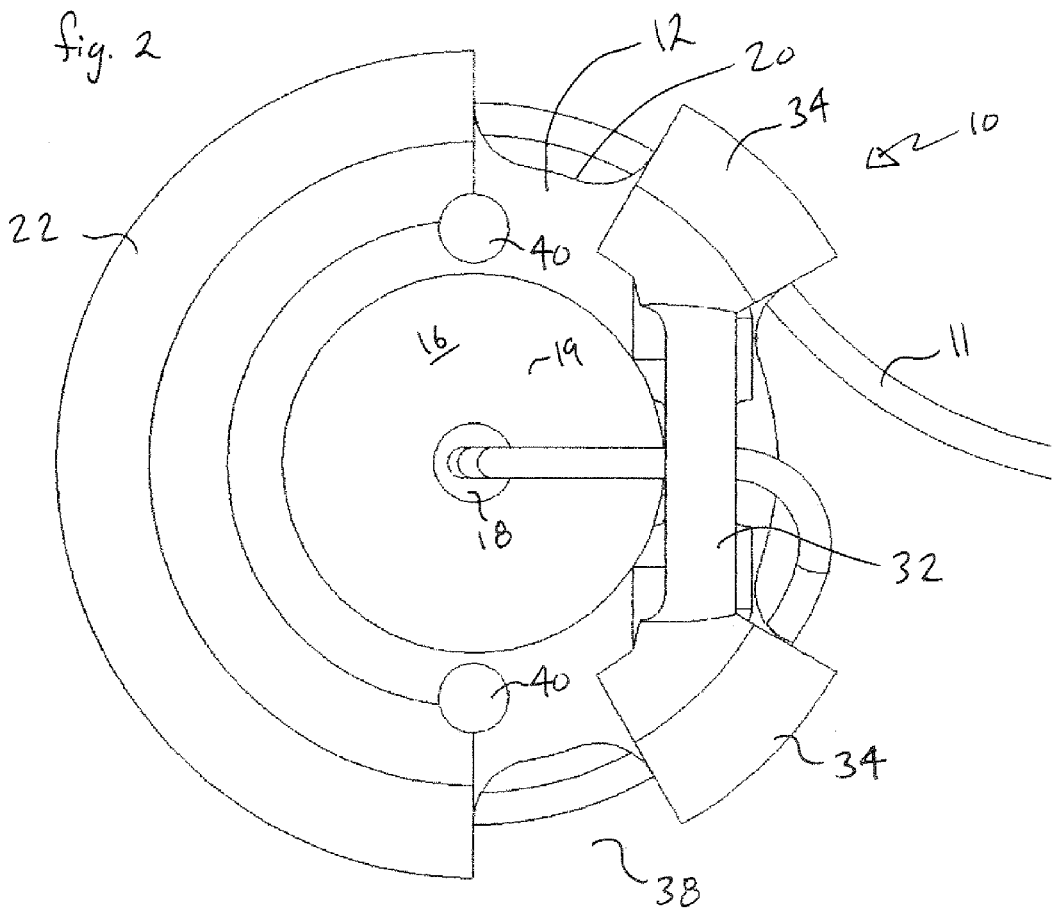
FIG. 2 is a top plan view of the lead-anchor, according to the first embodiment of the present invention, showing a representative lead in an anchored position exiting the flared passage and being secured within the peripheral lead-encapsulating structure.
Figure 5:
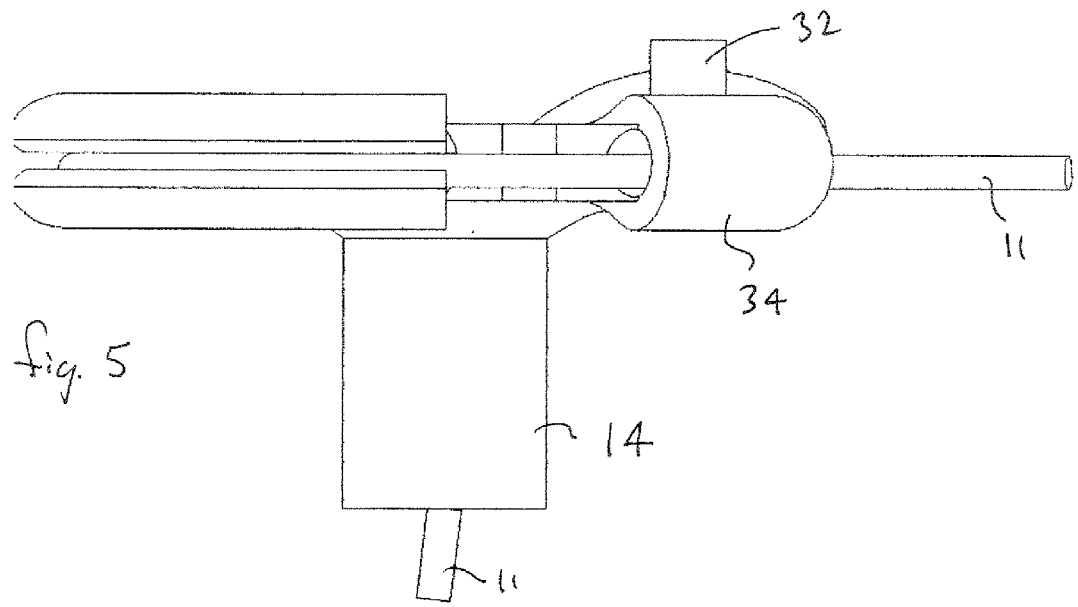
FIG. 5 is a side elevation view of the lead-anchor, according to the first embodiment of the present invention, showing details of the lead-encapsulating structure including an anchor sleeve and also the representative lead in the anchored position.
Figure 6:
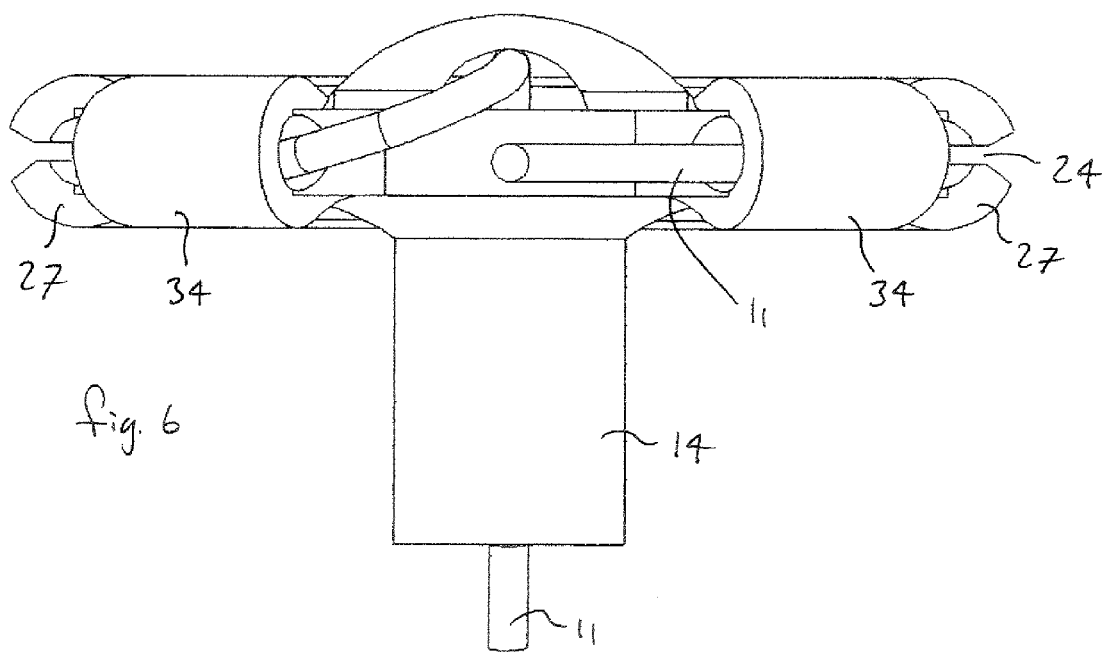
FIG. 6 is a front elevation view of the lead-anchor, according to the first embodiment of the present invention, showing details of the lead-encapsulating structure including an anchor bridge and with the representative lead in the anchored position.

As shown in FIGS. 1, 2, 4, 5, 6, and 7, rim plate 12 defines a periphery 20 to which a rim lead-holder 22 is integrally formed. As can be seen in FIG. 2, rim lead-holder 22 extends approximately 180 arc degrees around rim plate 12. Located along the entire 180 arc degree curved length of rim lead-holder 22 is a channel 24 that is defined by a passage 26 and a side slit 28. This rim lead-holder 22, also called a "middle tube" preferably extends between 90 and 270 arc degrees about the periphery 20. Passage 26, which includes entry/exit ends 27, is sized and shaped to snugly receive lead 11. Side slit 28 is formed integrally during the molding of anchor 10 and has a resting width that is less than the diameter of lead 11 so that a lead 11 can be effectively captured by passage 26 and held in place by the natural resiliency of the rim lead-holder 22. Side slit 28 preferably further includes opposing beveled or rounded outer edges 30. As can be appreciated by one skilled in the art, the purpose of side slit 28 is to provide quick access to passage 26 so that a surgeon may quickly press a lead 11 through side slit 28 and into the holding confines of passage 26. The purpose of the preferred beveled outer edges 30 is to help the surgeon guide the lead 11 along the length of the side slit 28 and to further encourage its quick entry into passage 26.

As shown in FIGS. 1, 2, 4, 6, and 7, rim plate 12 further includes an anchor bridge 32 which is preferably integrally formed along upper surface 21 of rim plate 12 and generally opposite rim lead-holder 20. The purpose of anchor bridge 32 is to receive and hold a lead 11 exiting the flared passage 16 and also to help encourage a relatively atraumatic transition of the exiting lead 11 to a more tangential trajectory that is coplanar with rim plate 12, as lead 11 is captured within passage 26. Lead 11 is gently directed to bend at the point of anchor bridge 32 and the resulting friction generated at this bend point will help hold lead 11 in a stable position about anchor 10 and thereby will discourage any dislodgement of its distal end from the target site located within the patient's brain.

As is illustrated in FIGS. 1 and 2, located between anchor bridge 32 and both entry/exit ends 27 of rim lead-holder 22 are positioned rim anchor sleeves 34. These sleeves are short anchoring structures that are integrally formed with rim plate 12. Each of these sleeves includes an arcuate passage 36 which is sized and shaped to receive lead 11 and which align with arcuate passage 26 of rim lead-holder 22. Rim anchor sleeves 34 are tubular in that they do not include a side slit, as rim-lead-holder 22 does. The purpose of rim anchor sleeves 34 is to provide a guided entry into and a guided exit from the passage 26 of rim channel 22. Anchor sleeves 34 prevent any tension of lead 11 from forcing the captured portion of lead 11 to dislodge itself from the friction hold of passage 26 through side slit 28.

As shown in FIGS. 1, 2, and 3, the relative size, shape and positions of rim lead-holder 22 and rim anchor sleeves 34 define spaces 38 therebetween. These spaces 38 offer the surgeon room to manipulate the end of the lead 11 and feed the same into passage 36 of anchor sleeves 34 and rim lead-holder 22 using a pair of hemostats or his or her fingers, as necessary.

Figure 8:
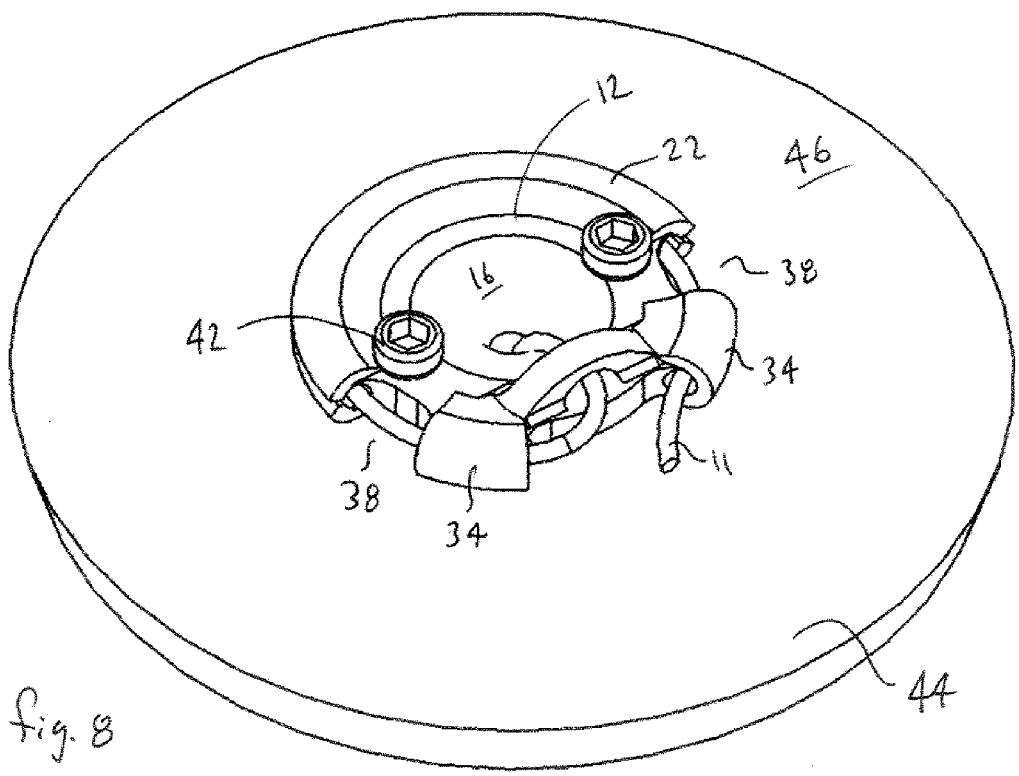
FIG. 8 is a perspective view of the lead-anchor, according to the first embodiment of the invention, showing the device fastened to a representative section of a patient's skull.

Referring now to FIGS. 1, 2, 8 and 9, rim plate 12 includes at least two opposing bores 40 that are sized and shaped to receive appropriate fasteners 42 for securing anchor 10 to the outside surface 44 of a patient's skull 46 (only a representative circular portion of a skull 46 is shown in FIG. 8 and 9). As shown in FIGS. 8 and 9, fasteners 42, when securing anchor 10 to skull 46 do not interfere with lead 11 as it is held in position about anchor 10. Fasteners 42 are preferably made from titanium (or any other biocompatible material that is preferably non-magnetic) and further includes any appropriate drive head, such as a square drive head, a Torx® drivehead, or an Allen drive head allowing the surgeon to confidently apply the required torque to penetrate the patient's skull 46 to secure the anchor thereto.

An important feature of the present invention is to provide not only an anchor for intracranially implanted lead wires or catheters, but also a transition point that smoothly and atraumatically redirects a perpendicularly-exiting lead 11 from a patient's skull to a path that is generally tangent to the patient's skull. This redirection allows any leads and catheters to exit the patient's skull and atraumatically bend so that they can be positioned under the patient's scalp in a manner that is more accommodating to the patient's movements and general life style. A patient can more easily hide their medical disposition if lead 11 can be guided close to their scalp without concern that any harm will come lead 11 or the pinpoint positioning of its distal end.

Anchor 10 is preferably made from a biocompatible polymer material including thermoplastic elastomers, such as Santoprene®, preferably having a durometer of about 87 Shore A. Anchor 10 may also be made from an implantable-grade radio-opaque, MRI-safe silicone rubber that preferably has a durometer of between 50 and 100 Shore A. The level of durometer should offer anchor 10 semi-rigidity, a level of flexibility that allows fasteners 42 to secure rim plate 12 firmly against the patient's skull 46 without causing the material to collapse and unduly deform under the compression forces of the tightened fasteners 42. If the material is made too flexible (e.g., a durometer less than 30 Shore A), fasteners 42 would merely deform the local areas of contact and the anchor 10 would not function properly and could slip entirely over the heads of the fasteners. If the material is made too rigid, anchor 10 would not properly conform to the curvature of the patient's skull 46 (or other irregularities found on the skull) and could fracture under the compressive forces as fasteners 42 are tightened. Another consideration in selecting an appropriate material for anchor 10 is that the material's coefficient of friction should be relatively high so that the material will form a high friction surface bond when contacting the lead.

Although not shown, Applicants contemplate an anchor 10 that is co-molded with two materials, each of a different durometer. In this arrangement, rim plate 12 is made from a more rigid material, while stem 14, anchor sleeves 34, anchor bridge 32 and rim lead-holder 22 are made from a more flexible (softer) material. This would allow sufficient support for anchor 10 to be secured to the patient's skull 46 and yet still provide soft sealing and lead-gripping structures to function effectively. As those skilled in the art will appreciate, well known co-molding and/or over-molding techniques could be used to manufacture this version of anchor 10.

As is well know, the thickness of a patient's skull 46 will vary depending on the location about the cranium and also from patient to patient. As discussed in greater detail below, before anchor 10 is fitted to the patient's skull 46, the thickness of the skull at the location of a burr hole 48 is measured and the hollow lower stem 14 is then cut (shortened) to an appropriate length based on the measurement. As is illustrated in the section view of FIG. 9, once cut, the stem 14 can be fitted within the burr hole and anchor 10 subsequently secured using fasteners 42. It can be appreciated that the outside cylindrical shape of stem 14 is similar to the shape of burr hole 48 formed in the patient's skull 46 so that a snug fit will be realized. It is preferable that the outside diameter of stem 14 actually be slightly larger than the inside diameter of the burr hole 48 so that when fitted, stem 14 of anchor 10 forms an even tighter fit within burr hole 48.

Figure 7:
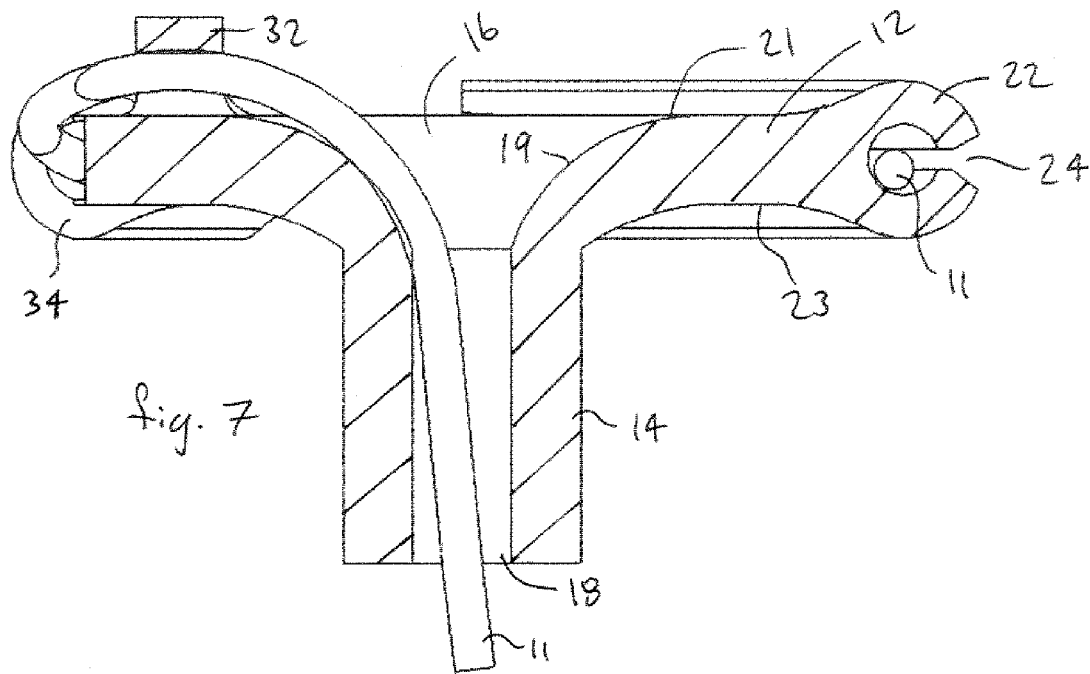
FIG. 7 is a sectional side elevation view of the lead-anchor, according to the first embodiment of the present invention, showing details of the flared passage, the stem and the rim plate, with the representative lead in the anchored position.

As shown in FIGS. 7 and 9, the shape of stem 14 (after being cut to the proper length) is such that anchor 10 can be advanced into burr hole 48 sufficiently that lower surface 23 of rim plate 12 contacts the outside surface 44 of the patient's skull 46. An appropriate biocompatible sealant or adhesive can be used to seal the space between the inside surface of the burr hole 48 and the outside surface of the stem 14. Such a sealant or adhesive may further be used between the outside surface 44 of the patient's skull 46 and the underside of rim plate 12 to provide an additional barrier against infection to the brain.

In use of this anchoring device, an incision is first made in a patient's scalp and the scalp is drawn from a desired drill-site. The surgeon uses a cranium perforator (or other drilling device) to create a carefully positioned burr hole 48. The outside diameter and depth of the burr hole 48 will vary from patient to patient and based on the location of the skull. Once burr hole 48 is created, the surgeon will verify the depth of the hole and will cut stem 14 of the present anchor 10 based on the measurement so that when fitted, the stem 14 will fit properly into the burr hole. Once cut to length, the surgeon inserts stem 14 of the present anchor 10 into burr hole until the lower surface 23 of rim plate 12 contacts the patient's skull. As described above, fasteners 42 are then inserted into bores 40 of rim plate 12 and the anchor 10 secured to the patient's skull. Of course, as can be appreciated by those skilled in the art, appropriate pre-drilling into the patient's skull may be required to effectively receive fasteners 42.

As mentioned above, prior to fitting the anchor 10 into burr hole 48, an appropriate sealant or adhesive may be applied to the lower surface 23 of rim plate 12 and possibly within the burr hole itself.

Once the present anchor 10 is fastened to the patient's skull, the surgeon uses instrumentation, usually including stereotactic guidance to insert and position the distal end of lead 11 to a target site within the patient's brain. Lead 11 passes through flared passage 16 (the wide end first) and then the smaller opening 18 located at the bottom of stem 14 before entering the patient's brain. Once the distal end of lead 11 reaches the desired target site within the brain, the proximal end of lead 11 (located outside the patient's skull) is threaded through anchor bridge 32, as shown in FIGS. 8 and 9, and then threaded into either anchor sleeve 34, and then guided into passage 26 by pressing lead 11 gently, but firmly through side slit 28. Once lead 11 follows around rim plate 12 into passage 26, the surgeon then threads its proximal end into the other anchor sleeve 34 and finally lead 11 is guided under the patient's scalp to exit therefrom at an appropriate opening located near the patient's neck. Finally, the patient's scalp is sutured closed over lead 11 and the entire anchor 10. Anchor 10 is made low profile and therefore can easily be accommodated under the patient's scalp.

Although not shown in the figures, to prevent or at least discourage infection to the patient's brain, an appropriate seal (such as a well known duckbill seal or a membrane seal) may be incorporated into the passage 16 to help seal this entry into the brain. In such instance, lead 11 must pass through the seal as it is advanced through passage 16 during initial insertion.

Once the anchor device 10 is firmly affixed to the user's skull, should the proximal end of lead 11 be pulled, the patient's scalp will function as a tension relief, but even if the tensile force reaches the anchor, the force will act mostly on the exiting anchor sleeve 34. Under such tensile forces, lead 11 will gently bind within passage 26, owing to the relatively large surface contact with lead 11. The end result is that the torturous (but atraumatic) path of lead 11 around anchor 10 prior to entering the patient's brain will help discourage any displacement of the distal end of the implanted lead 11 from the target site.

Referring now to FIGS. 10-13, a lead-anchor 100, according to a second embodiment is shown. Similar to the first embodiment shown in FIGS. 1-9 and described above, anchor 100 is similar to a funnel and includes a generally circular rim plate 102 and an integrally formed hollow lower stem 104. As before, this anchor 100 includes an internal flared passage 106 that has a small lower opening 108 that opens up to the larger diameter of the rim plate 102.

The purpose of this second embodiment is to show a skull-secured lead-anchor 100, which includes a different peripheral structure to hold a lead 11 in place. In this second embodiment, as described in greater detail below, the lead-holding peripheral structure includes at least two loops 150. Each loop 150 defines an opening 152 through which a lead 11 may pass. Loops 150 are made from a flexible material (preferably having a durometer between 30 and 80 Shore A, and more preferably between 30 and 50 Shore A) which allows a surgeon to easily spread open each loop wide enough to receive any connector (not shown) that may be secured to the proximal end of lead 11 (for example, a luer lock may be pre-secured to the proximal end of a catheter lead 11 or similarly, an appropriate electrical connector may be pre-secured to the end of an electrical lead wire 11). By making loops 150 very flexible, each loop can flex around the relatively large connector. The loops 150 should be made from a material that affords them sufficient stretchability and flexibility so that they can be selectively enlarged to accommodate large lead-connectors and yet have "memory" so that after stretched, the loops 150 will return to their original size, shape and orientation. Loops 150 should also not be so flexible that they do not provide some influence on the path of the lead that is laced through the loops about the periphery of the rim. In other words, the loops should gently force the lead to bend so that the lead follows a somewhat serpentine path about the anchor. This sinuous path is what helps hold the lead in place.

As can be seen in FIGS. 10-13, anchor 100 does not include any anchor bridge 32 as the above described first embodiment does. This second embodiment is meant to show an easy-to-manufacture and easy-to-use version. The anchor 100 shown in FIGS. 10-13 can be made using a simple planar type mold wherein no core plates or caming is required, as can be appreciated by those skilled in the art.

As already mentioned, the anchor 100 shown in FIGS. 10-13 has a different peripheral anchoring structure, but retains much of the structure of the above-described anchor 10, shown in FIGS. 1-9. For example, both embodiments of this anchor includes a rim plate (12, 102), a stem (14, 104), a flared passage (16, 106) and opposing bores (40, 140). The surgeon secures both anchors 10, 100, to the patient's skull 46 within a burr hole 48 in a similar manner, using fasteners 42. Once the anchor is secured to the patient's skull and the lead 11 is in the desired position, the surgeon secures lead 11 to anchor 100 differently. The surgeon merely threads the lead 11 through each loop 150 around the rim plate 102, like lacing a shoe. Since there is no anchor bridge 32 in this version, the surgeon can start with any of the loops and finish with any of the loops around rim plate 102.

Figure 12:
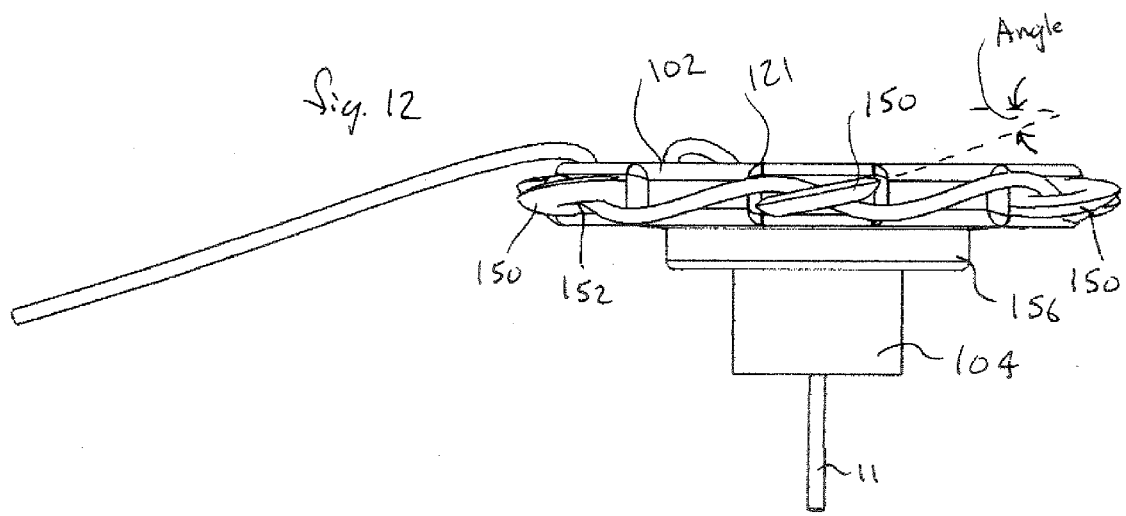
FIG. 12 is an elevation view of the lead-anchor, according to the second embodiment of the invention, with the lead wire in place.

As can be seen in FIG. 12, each loop 150 is formed within a plane that is angled with respect to upper surface 121 of rim plate 102. The preferred angle between these two planes is between 0 and 45 arc degrees, and more preferably between 10 and 20 arc degrees. This allows the surgeon a choice of holding friction. If lead 11 is laced through loops 150 in a clockwise direction, as shown in FIG. 10, the lead will experience an easier path since each angled loop is angled to provide a straighter path around rim plate 102. A lead laced within the loops in this direction will cause less trauma to the lead and therefore may be appropriate for a catheter. In contrast, a lead laced within loops 150 in the opposite (counter clockwise) direction, not shown, the lead would have to follow a more torturous path because in this direction each angled loop provides a less straight path forcing the lead to bend sharply below each loop before entering its respective opening 152. Of course the "trauma" to the lead 11 in either direction is still relatively minimal because the loops are preferably made from a flexible material and will be somewhat forgiving.

As shown in FIG. 10, each loop 150 preferably includes a cross-section that is wide so that opening 152 is relatively small and the surface area that contacts lead 11 when lead 11 is laced through loops 150 is maximized to increase holding friction. These loops 150 are designed to contort and bind against the surface of the laced lead when the lead is pulled, thereby preventing any tension generated at the proximal end of the lead from transmitting to the distal end within the brain. The loops 150 ensure that the distal end of the lead within the brain remains exactly at the target site.

The number, size and exact shape of loops 150 can vary to meet the exact requirements of the particular anchoring application. Of course, the angle of each loop 11 in this second embodiment shown in FIGS. 10-13 may also vary depending on the design particulars, as can the exact durometer of the material used to make either anchor.

Figure 11:
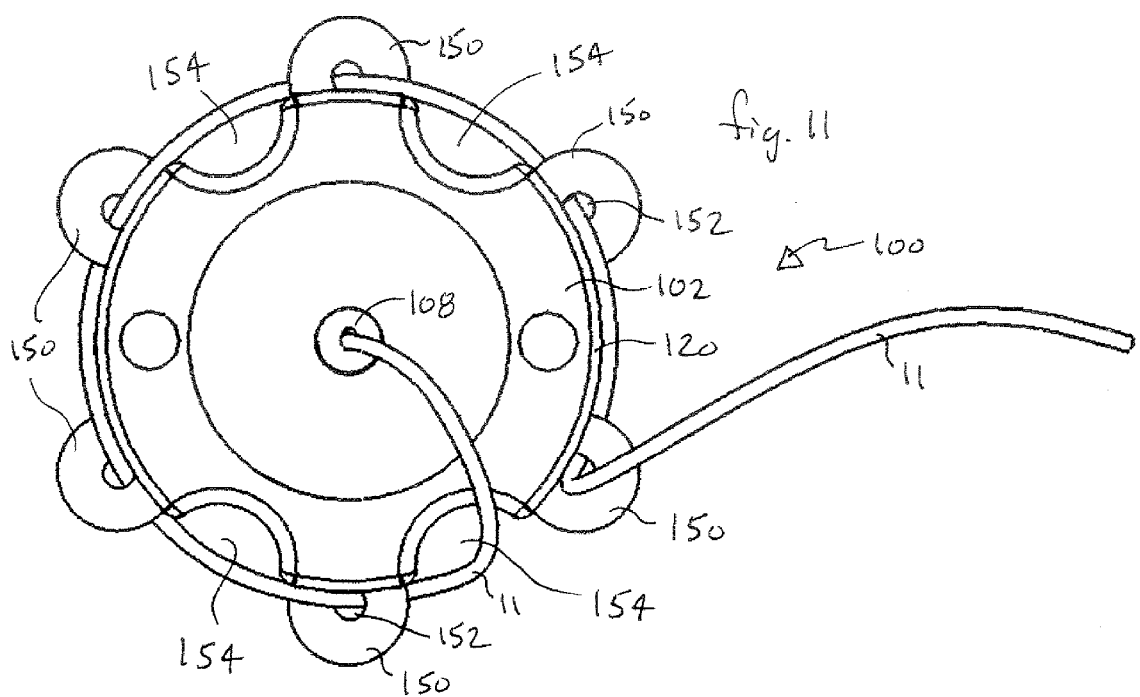
FIG. 11 is a top plan view of the lead-anchor, according to the second embodiment of the invention, with the lead wire in place.
Figure 13:
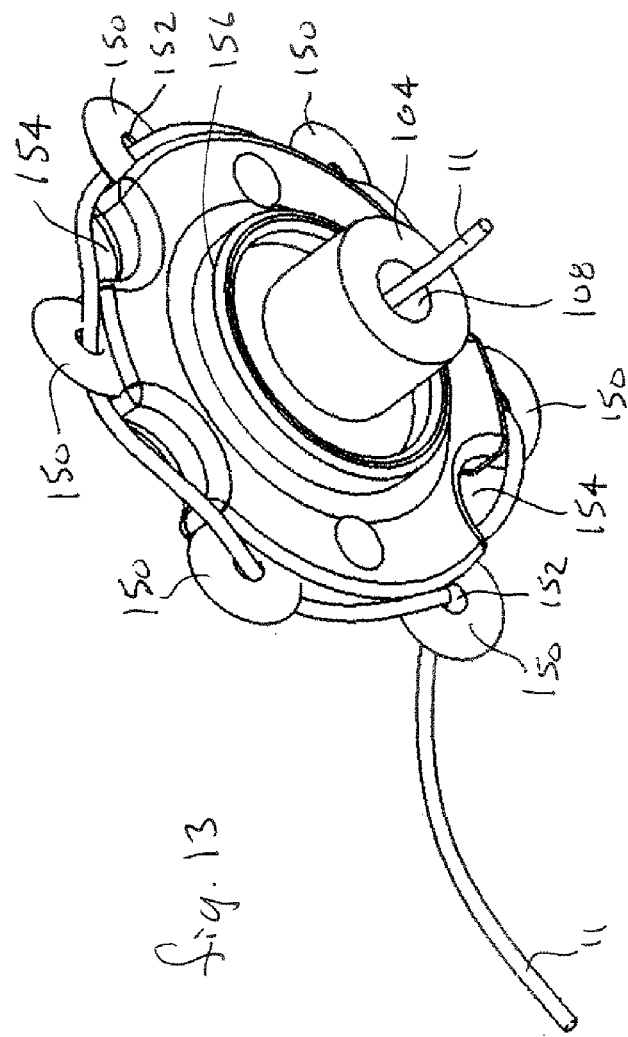
FIG. 13 is a perspective view of the lead-anchor, according to the second embodiment of the invention, showing details of the lower surface of the anchor and with the lead wire in place.

As can be seen in FIGS. 10, 11, and 13, rim plate 102 includes cutouts 154 along the periphery 120. The purpose of cutouts 154 is to offer a less sharp path for lead 11 to make the transition from vertically exiting flared passage 106 from the patient's brain to the more horizontal orientation about the rim plate 102 and through the loops 150. The lead 11 passes gently into any of the cutouts about the periphery 120 before entering any of the loops 150.

As shown in FIG. 13, the anchor 100 of this second embodiment further includes a sealing ring 156 located on the lower surface 123 of rim plate 102. This sealing ring 156 is meant to be integrally formed with rim plate and is preferably made from a very soft durometer material. The purpose of this sealing ring 156 is to first contact the surface of the patient's skull 46 and to create an effective seal about the burr hole 48. The sealing ring will compress against the patient's skull as the fasteners 42 are tightened, as can be appreciated by those skilled in the art.

What is claimed is:

1. An anchor system for securing a lead to a patient's skull, said lead being of the type that passes through a burr hole of said skull and that includes a distal end which is implanted within the patient's brain at a target site, the anchor system comprising:
    a cylindrical insert that is sized to fit snugly into said burr hole, said insert defining a lower end and an upper end, said insert including a passage that communicates said lower end with said upper end;
    a flange located about said insert at said upper end, said flange having an outer diameter that is larger than the inside diameter of said burr hole and defining a periphery;
    at least one clamp located along said periphery of said flange, said clamp being sized and shaped to snugly receive and clamp onto said lead;
    wherein said passage is flared from a first diameter at said lower end of said insert to a larger diameter at said upper end, said flared passage being adapted to receive said lead from said brain and further configured to allow said lead to atruamatically transition from a perpendicular path from said burr hole to a path that is generally tangential with respect to said flange, said clamp configured to receive and clamp onto said lead so that said lead is effectively anchored with respect to said patient's skull; and
    wherein said clamp includes a starting lead-receiving tube, a middle lead-receiving tube and an ending lead-receiving tube, said middle lead-receiving tube including a slit along its length so that a lead may be inserted into said middle tube through said slit, said middle tube being sized to snugly frictionally contact said lead when said lead is inserted into said middle tube.

2. The anchor system of claim 1 further including a transition loop located along said flange, said transition loop being sized and shaped to receive said lead between said flared passage and said clamp.

3. The anchor system of claim 2, wherein said transition loop is formed integrally with said flange.

4. The anchor system claim 1 wherein said insert is formed integrally with said flange.

5. The anchor system of claim 1, wherein said insert is made from a flexible biocompatible material.

6. The anchor system of claim 5, wherein said insert can be cut to length as desired.

7. The anchor system of claim 1, wherein said flared passage includes a cusp-shaped inner surface.

8. The anchor system of claim 1, wherein said flange includes at least one bore which is sized and shaped to receive a fastener that is appropriate for securement to a patient's skull.

9. The anchor system of claim 1, wherein said flange, said insert and said clamp are integrally formed from a semi-rigid biocompatible material.

10. The anchor system of claim 1, wherein said flange includes a lower surface, and further comprising a seal located on said lower surface, said seal being sized and shaped to contact the surface of the patient's skull when said anchor is secured to said skull.

11. The anchor system of claim 1, further comprising a mechanical fastener that is configured to selectively engage said patient's skull, and wherein said flange includes at least one opening that is sized and shaped to receive said mechanical fastener so that selective engagement of said mechanical fastener to said patient's skull effectively secures said anchor to said patient's skull.

12. The anchor system of claim 1, further comprising a layer of adhesive that is configured to bond to the patient's skull and the anchor material, said adhesive layer being positioned at selective locations on said patient's skull so that upon insertion of said anchor against said skull, said adhesive layer contacts a portion of said anchor and a portion of said skull, thereby securing said anchor to said skull.

13. The anchor system of claim 1, wherein said middle tube extends between 90 and 270 arc degrees around said periphery of said flange.

14. The anchor system of claim 13, wherein said middle tube extends about 180 arc degrees around said periphery of said flange.

15. The anchor system of claim 1, further comprising an anchor bridge disposed along an upper surface of said flange.

16. The anchor system of claim 1, further comprising an anchor bridge disposed along an upper surface of said flange.

* * * * *